United States Patent
Vigano' et al.

(10) Patent No.: US 9,708,343 B2
(45) Date of Patent: Jul. 18, 2017

(54) PROCESS FOR PREPARING RIFAXIMIN κ

(71) Applicant: CLAROCHEM IRELAND LTD., Dublin (IE)

(72) Inventors: Enrico Vigano', Lurago d'erba (IT); Renato Molteni, Giussano (IT); Simona Lanfranconi, Montano Lucino (IT); Massimiliano Arrighi, Luisago (IT); Fabio Gatti, Carimate (IT)

(73) Assignee: Clarochem Ireland Ltd., Dublin (IE)

( * ) Notice: Subject to any disclaimer, the term of this patent is extended or adjusted under 35 U.S.C. 154(b) by 0 days.

(21) Appl. No.: 14/908,777

(22) PCT Filed: Aug. 1, 2014

(86) PCT No.: PCT/EP2014/066592
§ 371 (c)(1),
(2) Date: Jan. 29, 2016

(87) PCT Pub. No.: WO2015/014984
PCT Pub. Date: Feb. 5, 2015

(65) Prior Publication Data
US 2016/0168166 A1      Jun. 16, 2016

(30) Foreign Application Priority Data
Aug. 2, 2013   (IT) .............................. MI2013A1307

(51) Int. Cl.
*C07D 498/22*          (2006.01)

(52) U.S. Cl.
CPC .................................. *C07D 498/22* (2013.01)

(58) Field of Classification Search
CPC .................................................. C07D 498/22
See application file for complete search history.

(56) References Cited

U.S. PATENT DOCUMENTS

2009/0082558 A1    3/2009  Kothakonda et al.

FOREIGN PATENT DOCUMENTS

| WO | 2009/108730 A2 | 9/2009 |
| WO | 2011/153444 A1 | 12/2011 |
| WO | 2011/156897 A2 | 12/2011 |
| WO | 2012/156951 A1 | 11/2012 |
| WO | 2013/027227 A1 | 2/2013 |

OTHER PUBLICATIONS

International Search Report for PCT/EP2014/066592 dated Jan. 22, 2015 (5 pages).

*Primary Examiner* — Bruck Kifle
(74) *Attorney, Agent, or Firm* — LeClairRyan, a Professional Corporation (57) ABSTRACT

The present invention relates to a process for obtaining rifaximin κ comprising the following steps: a) reacting rifamycin O with 2-amino-4-picoline in the presence of a solvent mixture comprising water and a solvent selected from methyl isobutylketone, ethylacetate and a water soluble solvent; b) obtaining a rifaximin solution by removing the aqueous phase; c) obtaining rifaximin κ from the rifaximin solution, wherein when the solvent is a water soluble solvent, either methyl isobutylketone or ethylacetate is further added in step a). In another aspect the process of the invention relates to a process for obtaining the crystalline form κ of rifaximin comprising the following steps: i) contacting rifaximin or a rifaximin solution with exclusively ethylacetate, ii) obtaining the rifaximin in crystalline form κ by removing ethylacetate.

6 Claims, 4 Drawing Sheets

PROCESS FOR PREPARING RIFAXIMIN κ

RELATED APPLICATIONS

This application is a national phase of Application No. PCT/EP2014/066592 filed Aug. 1, 2014, and claims priority from Italian Patent Application No. MI2013A001307 filed Aug. 2, 2013, both incorporated by reference in their entirety.

FIELD OF THE INVENTION

The present invention relates to a process for preparing rifaximin κ.

PRIOR ART

Rifaximin, IUPAC name: (2S,16Z,18E,20S,21S,22R, 23R,24R,25S,26S,27S,28E)-5,6,21,23,25-pentahydroxy-27-methoxy-2,4,11,16,20,22,24,26-octamethyl-2,7-(epoxy-pentadeca-[1,11,13]-trienimmino)-benzofuro-[4,5-e]-pirido-[1,2-α]-benzimidazol-1,15(2H)-dione,25-acetate, is the compound of formula (I):

Rifaximin is a broad-spectrum antibiotic belonging to the family of rifamycins, devoid of systemic activity. In view of its physicochemical properties, it is not adsorbed in the gastrointestinal tract and therefore exerts its antimicrobial action inside the gastrointestinal tract. Rifaximin therefore has applications in the treatment of diarrhoea and of microbial infections of the gastrointestinal tract typically caused by *E. coli*, a microorganism which, being incapable of passing through the mucosa of the gastrointestinal tract, remains in contact with the gastrointestinal fluids. Rifaximin also has applications for the treatment of irritable bowel syndrome, Crohn's disease, diverticulitis and for antibiotic prophylaxis preceding surgical operations on the intestines.

Rifaximin was obtained and described for the first time in the EP161534 starting from rifamycin O and 2-amino-4-picoline in the presence of ethanol/water and ascorbic acid/HCl to obtain raw rifaximin which is then treated with Ethanol/water to obtain crystallized rifaximin.

Polymorphic forms of rifaximin, and processes for their synthesis and purification, are described in various documents of the known art.

Rifaximin κ was firstly described in WO2012/156951. Such a crystalline form resulted to be more stable in the presence of humidity than the other known crystalline forms of rifaximin, thus enabling the storage, even for prolonged periods. Such a polymorph was obtained by a process starting from rifaximin comprising the following steps:—suspending or dissolving rifaximin in a 1,2-dimethoxyethane based solvent, recovering the product and drying to remove said 1,2-dimethoxyethane based solvent. In one of the embodiments of the invention 1,2-dimethoxyethane is used as the unique solvent of rifaximin, in other 1,2-dimethoxyethane is described as used in combination of n-heptane, methanol, acetonitrile, R—COO—R$^1$ esters wherein R and R$^1$ are independently C$_3$-C$_6$ alkyl radicals, and C$_3$-C$_7$ alkyl ketones, ethanol, isopropanol and water.

Despite the known process for obtaining rifaximin κ, which describes high yields of the polymorph, the need was however felt for new processes with high performance also in the purity of the polymorph and convenient from an industrial point of view.

SUMMARY OF THE INVENTION

The inventors of the present patent application have now identified a new process for obtaining rifaximin κ, wherein the addition of methyl isobutylketone or ethylacetate to water in the obtainment of rifaximin solution before the crystallization step allows to obtain a final rifaximin κ in high purity and yields in view of better conversion during the reaction between rifamycin O with 2-amino-4-picoline.

Therefore the present invention concerns a process for obtaining rifaximin κ comprising the following steps:
a) reacting rifamycin O with 2-amino-4-picoline in the presence of a solvent mixture comprising water and a solvent selected from methyl isobutylketone, ethylacetate and a water soluble solvent;
b) obtaining a rifaximin solution by removing the aqueous phase;
c) obtaining rifaximin κ from the rifaximin solution, wherein when the solvent is a water soluble solvent, either methyl isobutylketone or ethylacetate is further added in step a).

In a second aspect, the invention provides a one-pot process for preparing rifaximin κ comprising the following steps:
a) reacting rifamycin O with 2-amino-4-picoline in the presence of a mixture comprising water and ethylacetate;
b) obtaining a rifaximin solution in ethylacetate by removing the aqueous phase;
c) obtaining rifaximin κ from the rifaximin solution in ethylacetate through the removal of the ethylacetate.

Surprisingly, ethylacetate was shown to be an optimal solvent for obtaining rifaximin κ.

In accordance with a third aspect, the present invention provides for a process for obtaining the crystalline form κ of rifaximin comprising the following steps:
i) contacting rifaximin or a rifaximin solution with exclusively ethylacetate,
ii) obtaining the rifaximin in crystalline form κ by removing ethylacetate.

Either after step i) or after step b) a wet rifaximin with ethylacetate is obtained.

Figure 5:
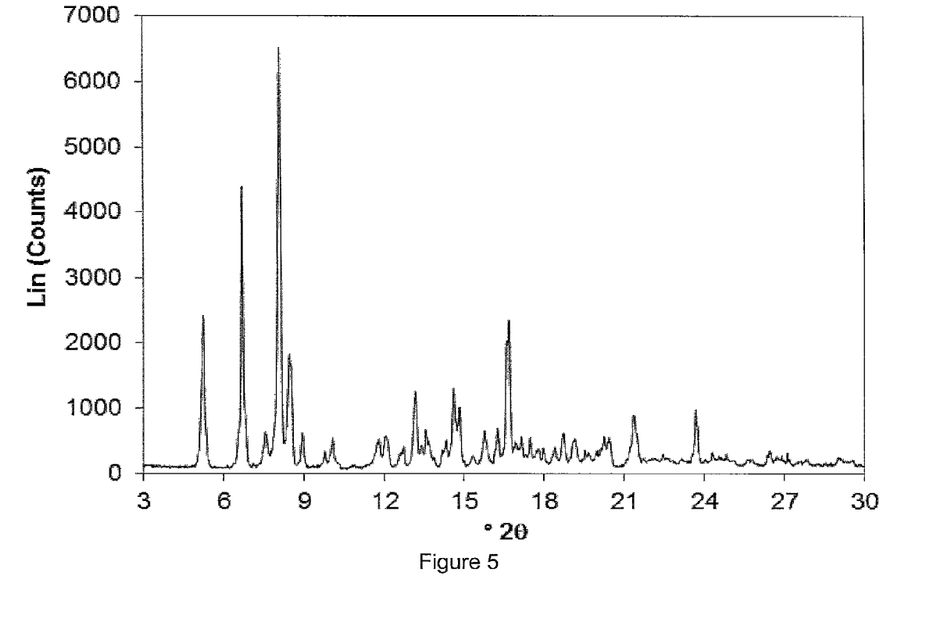
FIG. 5 shows a powder X-ray diffraction spectrum of the solvated rifaximin crystalline form of $2(C_{43}H_{51}N_3O_{11}).2(C_4H_8O_2).\frac{1}{2}(H_2O)$.

Further surprisingly, in a still further aspect, rifaximin wet with ethylacetate resulted to be a new solvated rifaximin crystalline form, which, as shown in FIG. 5 in a powder X-ray diffraction analysis shows peaks at values of angles 2θ of 5.23°, 6.70°, 7.57°, 8.09°, 8.49°, 8.95°, 11.78°, 12.08°, 13.17°, 14.62°, 14.80°, 15.78°, 16.24°, 16.64°, 19.13°, 21.38°, 23.70°.

The new solvated rifaximin crystalline form is obtained when the ethylacetate is is contacted to the rifaximin solution or to solid rifaximin for the obtainment of rifaximin κ. The rifaximin solution of step i) is preferably a solution of rifaximin in ethylacetate.

The crystalline form κ of rifaximin obtained according to the first aspect, the second aspect and the third aspect of the invention has purity higher than or equal to 90%, preferably ≥98%. This high purity guarantees that the crystalline form κ of rifaximin of the invention is in conformity with the commercial standards of rifaximin.

The process of the invention is extremely advantageous since it does not oblige to intermediate purification steps in order to isolate the crystalline form κ of rifaximin with requested purity. Such a purity of ≥90, more preferably ≥98% is very high and obtained with a limitative number of steps from the starting materials. Furthermore the process of the invention advantageously provides directly the crystalline form κ of rifaximin without requesting to isolate raw rifaximin preliminarily.

DETAILED DESCRIPTION OF THE INVENTION

The present invention concerns a process for obtaining rifaximin κ comprising the following steps:

a) reacting rifamycin O with 2-amino-4-picoline in the presence of a solvent mixture comprising water and a solvent selected from methyl isobutylketone, ethylacetate and a water soluble solvent;

b) obtaining a rifaximin solution by removing the aqueous phase;

c) obtaining rifaximin κ from the rifaximin solution, wherein when the solvent is a water soluble solvent, either methyl isobutylketone or ethylacetate is further added in step a).

In a first preferred embodiment of the invention either methyl isobutylketone or ethylacetate is the solvent of the solvent mixture of the reaction step a).

More preferably methyl isobutylketone is the mixture solvent of the reaction step a).

More preferably ethylacetate is the mixture solvent of the reaction step a). The new solvated rifaximin crystalline form is obtained when ethylacetate is the mixture solvent of step a) and is the solvent of the rifaximin solution of the step b) and c), for the obtainment of rifaximin κ. As stated above, the rifaximin wet with ethylacetate resulted to be a new solvated rifaximin crystalline form, which, as shown in FIG. 5 in a powder X-ray diffraction analysis shows peaks at values of angles 2θ of 5.23°, 6.70°, 7.57°, 8.09°, 8.49°, 8.95°, 11.78°, 12.08°, 13.17°, 14.62°, 14.80°, 15.78°, 16.24°, 16.64°, 19.13°, 21.38°, 23.70°.

In a second preferred embodiment of the invention the reaction solvent mixture consists of water and a water soluble solvent. In this preferred second embodiment either methyl isobutylketone or ethylacetate is subsequently added to the reaction solution in step a).

In step a) the use of either methyl isobutylketone or ethylacetate directly in solvent mixture of the reaction between rifamycin O and 2-amino-4-picoline (first preferred embodiment of the invention) or in a subsequent time the addition of either methyl isobutylketone or ethylacetate to the reaction solution made of water/water soluble solvent mixture (second preferred embodiment of the invention) allows to obtain two phases: an organic phase containing raw rifaximin and based on methyl isobutylketone or ethylacetate and a water phase containing unreacted 2-amino-4-picoline and other hydrophilic impurities of the reaction between rifamycin O and 2-amino-4-picoline.

Without being bound to any theory, the inventors deem that the final rifaximin κ is obtained in high yields and high purity in view of the presence of this two-phase system of water and methyl isobutylketone or ethylacetate.

In the second embodiment of the invention when the solvent of the solvent mixture is a water soluble solvent, this solvent is preferably selected from the group consisting of ethanol, acetonitrile and acetone, more preferably acetonitrile.

After step a) two separated phases are present: an organic phase solution of either methyl isobutylketone or ethylacetate comprising rifaximin and an aqueous phase comprising hydrophilic impurities of the reaction of step a). In step b) the rifaximin solution is obtained by removing the aqueous phase from the two-phase system.

Preferably after having removed the aqueous phase the rifaximin solution in ethylacetate or methyl isobutylketone is anhydrificated. The water still present in the rifaximin solution of methyl isobutylketone or ethylacetate is removed by azeotropic distillation.

The obtainment step c) of rifaximin κ from the rifaximin solution obtained by step b) can be carried out as described in WO2012/156951 starting from non-dried rifaximin in methyl isobutylketone or ethylacetate. In this case the process provides for the addition of 1,2-dimethoxyethane or a solvent mixture based on 1,2-dimethoxyethane in order to precipitate rifaximin κ from the rifaximin solution.

Preferably the obtainment step c) is carried out by seeding in the rifaximin solution a low amount of the crystalline form κ of rifaximin.

In the first preferred embodiment of the invention wherein the reaction solvent mixture comprises methyl isobutylketone and water or in the second preferred embodiment when isobutylketone is further added in step a), the rifaximin solution of step b) is a rifaximin solution of methyl isobutylketone and the polymorph rifaximin κ can also be advantageously obtained with the addition in step c) of ethylacetate, thus obtaining a wet rifaximin which is preferably converted to rifaximin κ by filtration and drying. As stated above, the rifaximin wet with ethylacetate resulted to be a new solvated rifaximin crystalline form, which, as shown in FIG. 5 in a powder X-ray diffraction analysis shows peaks at values of angles 2θ of 5.23°, 6.70°, 7.57°, 8.09°, 8.49°, 8.95°, 11.78°, 12.08°, 13.17°, 14.62°, 14.80°, 15.78°, 16.24°, 16.64°, 19.13°, 21.38°, 23.70°.

In the first preferred embodiment of the invention wherein the reaction solvent mixture comprises more preferably ethylacetate and water or in the second preferred embodiment when ethylacetate is further added in step a), the crystalline form rifaximin κ is obtained more advantageously from the ethylacetate rifaximin solution of step b). As stated above the rifaximin wet with ethylacetate resulted to be the new solvated rifaximin crystalline form, which, as shown in FIG. 5 in a powder X-ray diffraction analysis shows peaks at values of angles 2θ of 5.23°, 6.70°, 7.57°, 8.09°, 8.49°, 8.95°, 11.78°, 12.08°, 13.17°, 14.62°, 14.80°, 15.78°, 16.24°, 16.64°, 19.13°, 21.38°, 23.70°. From the ethylacetate solution of step b) rifaximin κ is preferably obtained through filtration and removal of ethylacetate by drying.

In the most preferred embodiment in step a) the solvent mixture comprises water and ethylacetate, the rifaximin solution is a solution of rifaximin in ethylacetate and the crystalline form κ of rifaximin is obtained advantageously from the ethylacetate rifaximin solution. This process is carried out advantageously with a single solvent, which is ethylacetate.

Therefore in a second aspect the invention concerns a one-pot process comprising the following steps:
a) reacting rifamycin O with 2-amino-4-picoline in the presence of a mixture comprising water and ethylacetate;
b) obtaining a rifaximin solution in ethylacetate by removing the aqueous phase;
c) obtaining rifaximin κ from the rifaximin solution in ethylacetate through the removal of the ethylacetate.

Surprisingly, ethylacetate was shown to be an optimal solvent for obtaining rifaximin κ.

This more preferred embodiment of the invention is extremely advantageous from an industrial point of view, since a single solvent is used and the final rifaximin κ is obtained in high yield and high purity.

The ethylacetate solvent resulted to be very advantageous for obtaining rifaximin κ as above explained. The present inventors tried to use ethylacetate in order to obtain rifaximin κ and surprisingly found out that rifaximin κ can be obtained from any kind of rifaximin by using ethylacetate. Ethylacetate showed to be the best solvent for obtaining rifaximin κ.

In a third aspect the invention hence concerns a process for obtaining the crystalline form κ of rifaximin comprising the following steps:
i) contacting rifaximin or a rifaximin solution with exclusively ethylacetate,
ii) obtaining the rifaximin in crystalline form κ by removing ethylacetate.

The starting rifaximin of the third aspect of the invention may be amorphous or in the form of any of its previously known polymorphs or mixtures of known polymorphs and/or with percentages of amorphous rifaximin. The initial product may be acquired, or prepared just before the process of the invention.

Preferably the rifaximin solution of step i) is a solution of rifaximin in ethylacetate.

The step ii) of the obtainment of the rifaximin κ by removal of ethylacetate comprises preferably a substep of filtration of the solution of the rifaximin in ethylacetate and a subsequent step of drying. This two substeps are also preferred in the first aspect and in the second aspect of the invention wherein a rifaximin solution in ethylacetate is obtained.

Without being bound to any theory the present inventors found that the use of ethylacetate makes the drying step ii) easier and allows a better control of the final granulometry of the rifaximin κ.

The third aspect of the invention resulted extremely advantageous since with a single solvent, it was possible to manage the crystallization conditions with the surprising effect to manage the particle size distribution. Furthermore, in a preferred embodiment of the third aspect of the invention the step i) was carried out by contacting ethylacetate heated at a temperature in the range from 40 to 60° C., preferably 50° C., thus obtaining rifaximin in crystalline form κ after step ii) with high yield, high purity and with a particle size distribution (PSD) equal to or higher than 250 μm.

As stated above the rifaximin wet with ethylacetate resulted to be the new solvated rifaximin crystalline form.

The wet rifaximin, obtained with the contacting step i) with ethyl acetate was characterized. The crystals of the wet rifaximin have been analyzed by TGA, XRPD, and single crystal X-ray diffraction and the characterization surprisingly revealed that a solvated rifaximin crystalline form was obtained having crystal characterization different from the final obtained rifaximin κ.

In a still further aspect, the invention hence relates to a new solvated rifaximin crystal, which, as shown in FIG. 5 in a powder X-ray diffraction analysis shows peaks at values of angles 2θ of 5.23°, 6.70°, 7.57°, 8.09°, 8.49°, 8.95°, 11.78°, 12.08°, 13.17°, 14.62°, 14.80°, 15.78°, 16.24°, 16.64°, 19.13°, 21.38°, 23.70°.

Specifically, the following cell values of the solvated rifaximin were identified:

| | |
|---|---|
| Molecular content | $2(C_{43}H_{51}N_3O_{11}) \cdot 2(C_4H_8O_2) \cdot \frac{1}{2}(H_2O)$ |
| Formula | $C_{94}H_{119}N_6O_{26.5}$ |
| M | 1756.95 |
| dimension [mm] | 0.25 × 0.25 × 0.12 |
| crystal system | orthorhombic |
| space group | $P\ 2_12_12_1$ (no. 19) |
| a [Å] | 16.1303(10) |
| b [Å] | 23.0956(15) |
| c [Å] | 24.7584(16) |
| = = [°] | 90 |
| V [Å$^3$] | 9223.5(10) |

The present invention will now be described with reference to the following examples, which are provided for purely illustrative purposes, and must not be understood in a sense limiting the invention.

Example 1

Solvent Mixture with Acetonitrile/Water

Water (57 ml) was charged into a four neck round bottom flask, at 20-25° C., under nitrogen atmosphere, followed by rifamycin-O (30.0 g), 2-Amino-4-picoline (12.91 g) and acetonitrile (43 ml). The mixture was heated to 50±5° C. and hold at that temperature for 4 hours. The mixture was cooled to 20-25° C., ascorbic acid (0.79 g) was added and 37% HCl was added until pH<2.0. Methyl isobutylketone (80 ml) was added and the mixture was heated to 60±5° C. The lower aqueous layer was separated and the organic layer was washed with water (10 ml) at 50±5° C. and the lower aqueous layer was separated. The organic layer was distilled under vacuum until collecting 43 ml of distillate. Methyl isobutylketone (40 ml) was added, distillation under vacuum was performed until collecting 18 ml of distillate. The solution was heated to 70±5° C. and 1,2-dimethoxyethane (30 ml) was added. The mixture was seeded with rifaximin κ-form, hold at that temperature for 1 h, 1,2-dimethoxyethane (30 ml) was added and the mixture was cooled to 20-25° C. The mixture was hold at that temperature for at least 3 hours, filtered and washed with 1,2-dimethoxyethane (30 ml). The solid wet obtained was dried under vacuum at 90° C., to give 25.7 g of rifaximin κ-form. Yield: 82.18%, HPLC purity: 98.86%.

Example 2

Solvent Mixture with Ethanol/Water

Water (57 ml) was charged in a four neck round bottom flask, at 20-25° C., under nitrogen atmosphere, followed by rifamycin-O (30.0 g), 2-Amino-4-picoline (12.91 g) and ethanol (43 ml). The mixture was heated to 50±5° C. and hold at that temperature for 4 hours. The mixture was cooled to 20-25° C., ascorbic acid (0.79 g) was added and 37% HCl was added until pH<2.0. Methyl isobutylketone (80 ml) was added and the mixture was heated to 50±5° C. The lower aqueous layer was separated and the organic layer was washed with water (10 ml) at 50±5° C. and the lower aqueous layer was separated. The organic layer was distilled under vacuum until collecting 48 ml of distillate and methyl isobutylketone (40 ml) was added. Distillation under vacuum was performed again until collecting 35 ml of distillate. The temperature was adjusted to 55±5° C., 1,2-dimethoxyethane (30 ml) was added and the mixture was seeded with rifaximin κ-form. The mixture was hold at that temperature for 1 h, additional 1,2-dimethoxyethane (30 ml) was added and then the mixture was cooled to 20-25° C. The mixture was hold at 20-25° C. for at least 3 hours, filtered and washed with 1,2-dimethoxyethane (40 ml). The solid wet obtained was dried under vacuum at 90° C., to give 25.96 g of rifaximin κ-form. Yield: 83.01%; HPLC: 98.26%.

Example 3

Solvent Mixture with Methyl Isobutylketone/Water

In a four neck round bottom flask, at 20-25° C., under nitrogen atmosphere, rifamycin-O (30.0 g), 2-Amino-4-picoline (12.91 g), water (50 ml) and methyl isobutylketone (80 ml) were charged. The mixture was heated to 50±5° C. and hold at that temperature for 4 hours. The mixture was cooled to 20-25° C., ascorbic acid (0.79 g) was added and 37% HCl was added until pH<2.0. The aqueous layer was separated at 20-25° C. and the organic layer was washed with water (30 ml). Methyl isobutylketone (30 ml) was added and distillation was performed under vacuum until collecting 30 ml of distillate. The temperature was adjusted to 50±5° C., 1,2-dimethoxyethane (50 ml) was added and the mixture was seeded with rifaximin-κ form. The mixture was cooled to 20-25° C., hold at that temperature for at least 3 hours, filtered and washed with 1,2-dimethoxyethane (40 ml). The solid wet obtained was dried under vacuum at 90° C. to give 21.15 g of rifaximin κ-form. Yield: 67.65%.

Example 4

Solvent Mixture with Acetone/Water

Water (57 ml) was charged into a four neck round bottom flask, at 20-25° C., under nitrogen atmosphere, followed by rifamycin-O (30.0 g) 2-Amino-4-picoline (12.91 g) and acetone (43 ml). The mixture was heated to 50±5° C. and hold at that temperature for 4 hours. The mixture was cooled to 20-25° C., ascorbic acid (0.79 g) was added, Methyl isobutylketone (80 ml) was added and 37% HCl was added until pH<2.0. The mixture was heated to 50±5° C., the lower aqueous layer was separated, water (10 ml) was added and the lower aqueous layer was separated. The organic layer was distilled under vacuum until collecting 43 ml of distillate, methyl isobutylketone (40 ml) was added and distillation under vacuum was performed until collecting 20 ml of distillate.

The solution was heated to 70±5° C. and 1,2-dimethoxyethane (30 ml) was added. The mixture was seeded with rifaximin κ-form, hold at that temperature for 1 h, 1,2-dimethoxyethane (30 ml) was added and the mixture was cooled to 20-25° C. The mixture was hold at that temperature for at least 3 hours, filtered and washed with 1,2-dimethoxyethane (40 ml). The solid wet obtained was dried under vacuum at 90° C., to give 24.4 g of Rifaximin κ-form. Yield: 78.03%. HPLC purity: 98.32%.

Example 5

Solvent Mixture with Ethanol/Water

Water (57 ml) was charged in a four neck round bottom flask, at 20-25° C., under nitrogen atmosphere, followed by rifamycin-O (30.0 g), 2-Amino-4-picoline (12.91 g) and ethanol (43 ml). The mixture was heated to 50±5° C. and hold at that temperature for 4 hours. The mixture was cooled to 20-25° C., ascorbic acid (0.79 g) was added and 37% HCl was added until pH<2.0. Methyl isobutylketone (80 ml) was added and the mixture was heated to 50±5° C. The lower aqueous layer was separated and the organic layer was washed with water (10 ml) at 50±5° C. and the lower aqueous layer was separated. The mixture was concentrated to residue by distillation under vacuum, ethylacetate (150 ml) was added. The mixture was distilled under vacuum until collecting 60 ml of distillate; ethylacetate (210 ml) was added, the mixture was cooled to 20-25° C. The mixture was hold at 20-25° C. for 18 h, then cooled to 0-5° C., hold at that temperature for 2 hours, filtered and washed with ethylacetate (40 ml). The solid wet obtained was dried under vacuum at 90° C., to give 9.82 g of rifaximin κ-form. Yield: 31.40%. HPLC purity: 96.48%.

Example 6

Crystallization from Methyl Isobutylketone/Ethylacetate

Rifaximin (15 g) was dissolved in methyl isobutylketone (45 ml) at 20-25° C. Ethylacetate (30 ml) was added. After 2 hours additional ethylacetate was added (15 ml).

The mixture was hold at 20-25° C. for 18 h, then filtered and washed with ethylacetate (15 ml) to give a wet material that was dried under vacuum at 90° C. to give 12.16 g of rifaximin κ-form. Yield: 81.10%.

Example 7

Crystallization from Ethylacetate

Rifaximin (15 g) was dissolved in ethylacetate (45 ml) at 20-25° C. The mixture was hold at 20-25° C. for 18 h, then filtered and washed with ethylacetate (15 ml) to give a wet material that was dried under vacuum at 90° C. to give 13.76 g of rifaximin κ-form. Yield: 91.73%. PSD: d90<100 μm.

Example 8

Crystallization from Ethylacetate

Figure 1:
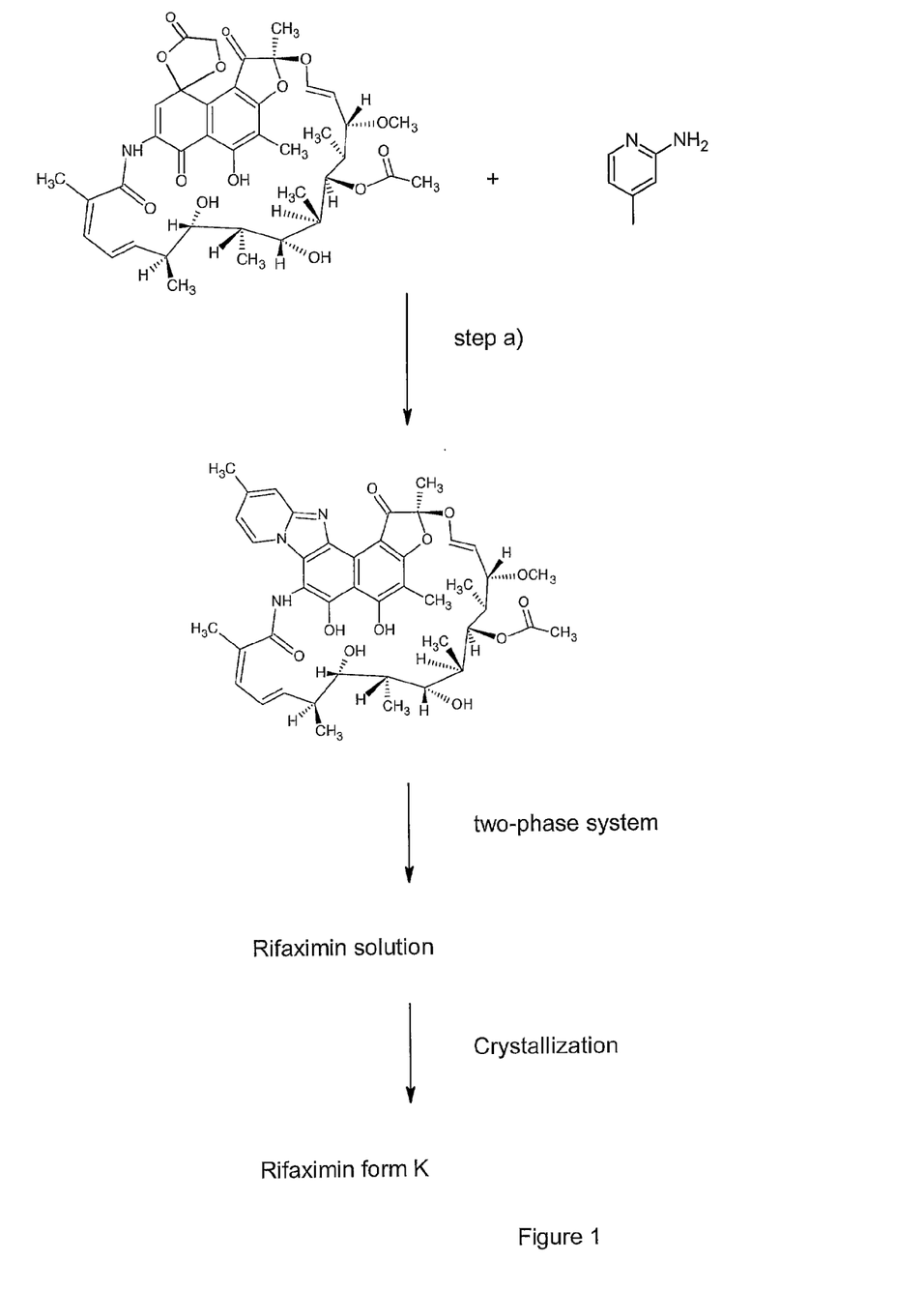
FIG. 1 shows is a scheme of the process of the invention.
Figure 2:
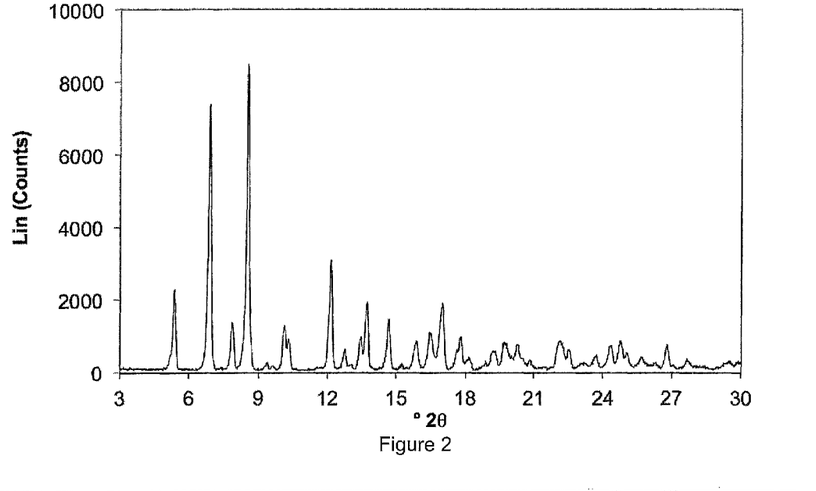
FIG. 2 shows a powder X-ray diffraction spectrum of the crystalline form κ obtained in the example 8 of the invention.

In a four neck round bottom flask, under nitrogen atmosphere, ethyl acetate (150 ml) was charged and heated to 50±2° C. Rifaximin (20.00 g) was charged affording a red solution. The mixture was hold at 50±2° C. for 2 hours. Additional Rifaximin (7.50 g) was added. The mixture was hold at 50±2° C. for 30 minutes then additional Rifaximin (7.50 g) was added. The mixture was hold at 50±2° C. for 30 minutes then additional Rifaximin (7.50 g) was added. The mixture was hold at 50±2° C. for 30 minutes then additional Rifaximin (7.50 g) was added. Ethyl acetate (50 ml) was added while maintaining 50±5° C. Distillation was performed until collecting 100 ml of solvent. Ethyl acetate (50 ml) was added while maintaining 75±5° C. Distillation was performed until collecting 50 ml of solvent. Ethyl acetate (100 ml) was added while maintaining 75±5° C. and then the mixture was cooled to 22±2° C. The mixture was hold at 22±2° C. for at least 3 hours, then filtered and washed with ethyl acetate (40 ml) to give 47.99 g of wet rifaximin. Wet rifaximin was dried at 90° C. under vacuum, to give 47.50 g of Rifaximin κ. HPLC purity: 99.50%. PSD: d90>250 μm. Rifaximin κ, obtained from ethyl acetate according to Example 8, was analyzed by XRPD. X-Ray diffraction pattern (CuKα radiation; voltage of 40 kV and current of 40 mA) was collected with a powder diffractometer Bruker D5005 (Siemens, Germany) equipped with monochromator and scintillator counter. The spectrum was recorded in the step scan mode (step: 0.02°; counting time: 5 s) in the angular range 2θ=3-30° in air at room temperature. X-Ray diffraction pattern is shown in FIG. 2. As it is evident the XRPD spectrum of the rifaximin obtained by Example 8 was the same as in WO2012/156951 thus confirming it was rifaximin κ.

Rifaximin wet, obtained from ethyl acetate according to Example 8, was characterized. The crystals of the wet rifaximin obtained in such a way have been analyzed by TGA, XRPD, and single crystal X-ray diffraction.

Figure 3:
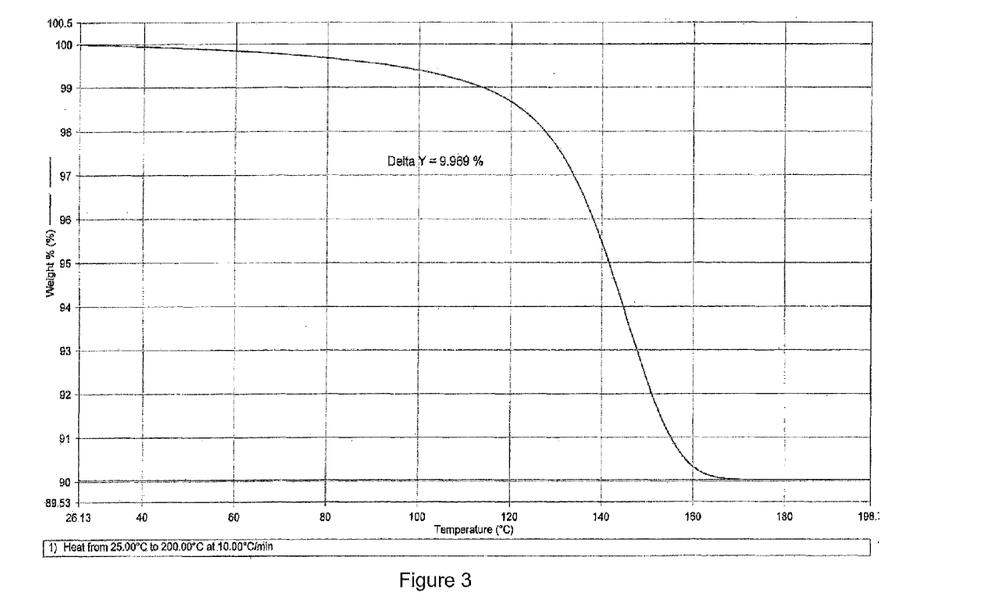
FIG. 3 shows the TGA spectrum of the solvated rifaximin crystalline form $2(C_{43}H_{51}N_3O_{11}).2(C_4H_8O_2).\frac{1}{2}(H_2O)$.
Figure 4:
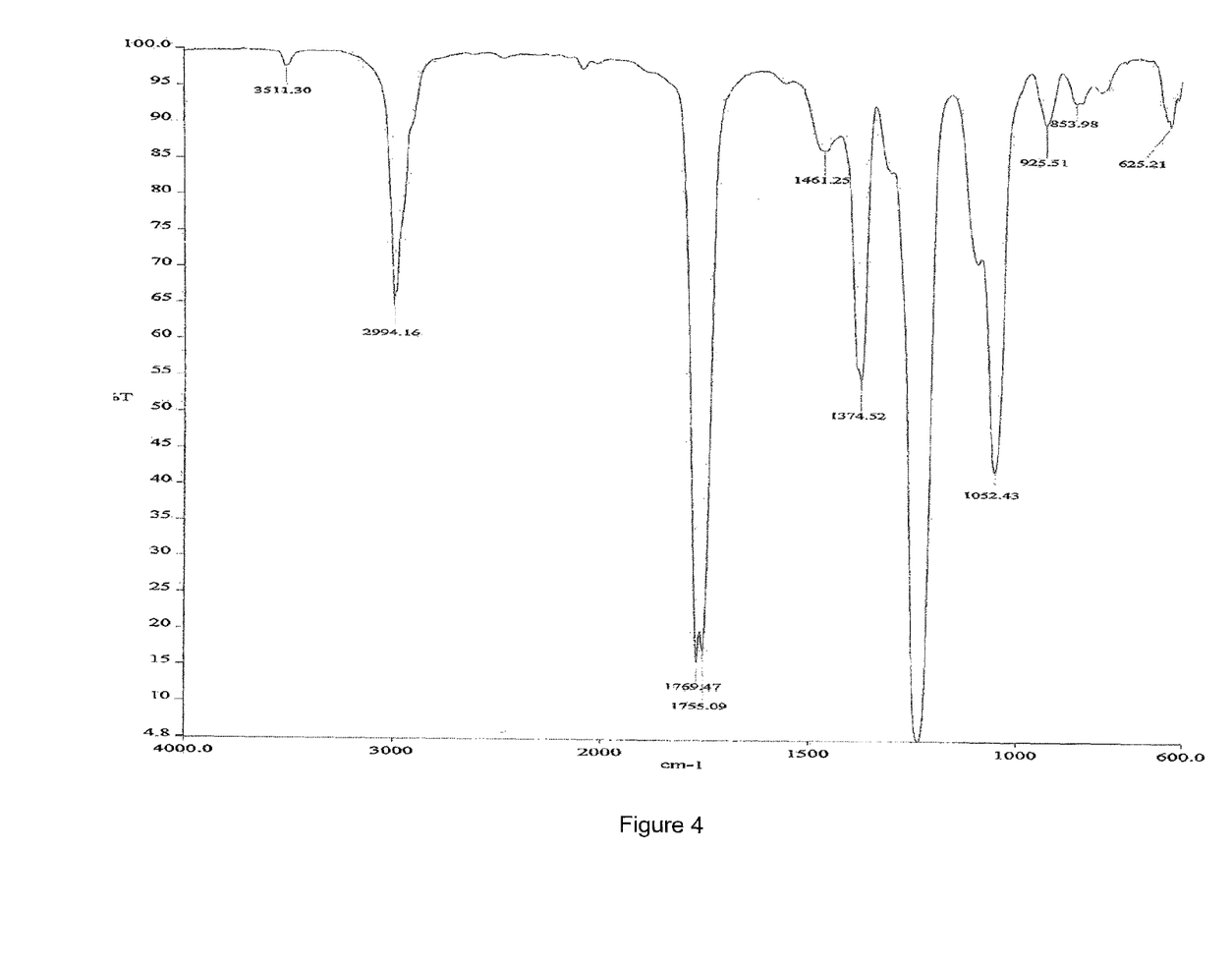
FIG. 4 shows the FT-IR spectrum of the solvated rifaximin crystalline form $2(C_{43}H_{51}N_3O_{11}).2(C_4H_8O_2).\frac{1}{2}(H_2O)$.

TGA was carried out with a PerkinElmer Pyris 1 TGA instrument, interfaced with a SpectrumOne FT-IR; temperature gradient 10° C./min. The results of the analysis showed a weight loss of 9.97% over the temperature range from 25 to 200° C. (FIG. 3). Via the FT-IR interface, the spectra of the gases emitted by the sample were continuously acquired during heating in TGA, and it was revealed that the weight loss could be ascribable for the most part to emission of the solvent ethyl acetate (FIG. 4).

X-Ray diffraction pattern (CuKα radiation; voltage of 40 kV and current of 40 mA) was collected with a powder diffractometer Bruker D5005 (Siemens, Germany) equipped with monochromator and scintillator counter. The spectrum has been recorded in the step scan mode (step: 0.02°; counting time: 5 s) in the angular range 2θ=3-30° in air at room temperature. X-Ray diffraction pattern is shown in FIG. 5, while the position and intensity of the relevant peaks is shown in Table 1.

Features of the diffractometer used in the single crystal X-ray diffraction study are summarized in Table 2, while the collected crystal data are listed in Table 3.

TABLE 1

| Angle (2θ) | d value (Å) | Intensity (%) |
| --- | --- | --- |
| 5.23 | 16.88622 | 39.9 |
| 6.70 | 13.18052 | 72.2 |
| 7.57 | 11.67468 | 10.5 |
| 8.09 | 10.92394 | 100 |
| 8.49 | 10.40798 | 30.4 |
| 8.95 | 9.87611 | 10.3 |
| 11.78 | 7.50638 | 7.9 |

TABLE 1-continued

| Angle (2θ) | d value (Å) | Intensity (%) |
| --- | --- | --- |
| 12.08 | 7.31854 | 9.5 |
| 13.17 | 6.71564 | 20.7 |
| 14.62 | 6.05498 | 21.6 |
| 14.80 | 5.97954 | 16.9 |
| 15.78 | 5.6119 | 10.8 |
| 16.24 | 5.45348 | 11.4 |
| 16.64 | 5.32324 | 38.9 |
| 19.13 | 4.63483 | 8.9 |
| 21.38 | 4.15294 | 14.8 |
| 23.70 | 3.75148 | 16.3 |

TABLE 2

| | |
| --- | --- |
| instrument type | single-crystal automatic diffractometer |
| instrument name | Bruker-AXS SMART-Apex |
| goniometer geometry | three circle, fixed chi |
| temperature of working | ambient temperature |
| X-ray source | sealed Mo X-ray tube |
| X-ray generator parameter | 50 kV × 30 mA, 1500 W |
| X-ray monochromatic radiation selected | Mo Kα, λ = 0.71073 Å |
| X-ray monochromator | graphite |
| X-ray detector type | bidimensional CCD plate |

TABLE 3

| | |
| --- | --- |
| Molecular content | 2($C_{43}H_{51}N_3O_{11}$)•2($C_4H_8O_2$)•½($H_2O$) |
| Formula | $C_{94}H_{119}N_6O_{26.5}$ |
| M | 1756.95 |
| dimension [mm] | 0.25 × 0.25 × 0.12 |
| crystal system | orthorhombic |
| space group | P 212121 (no. 19) |
| a [Å] | 16.1303(10) |
| b [Å] | 23.0956(15) |
| c [Å] | 24.7584(16) |
| = = [°] | 90 |
| V [Å$^3$] | 9223.5(10) |

The invention claimed is:

1. A process for obtaining a crystalline form κ of rifaximin characterized by a powder XRD spectrum with peaks at values of the angle 2θ of 5.3°, 6.8°, 7.8°, 8.5°, 9.3°, 10.1°, 10.3°, 12.1°, 12.7°, 13.4°, 13.7°, 14.6°, 15.3°, 15.8°, 16.4°, 16.9°, 17.7°, 18.0°, 18.8°, 19.2°, 19.7°, 20.3° and 22.1° comprising:
   contacting (i) solid rifaximin, (ii) a solution of rifaximin in ethylacetate, or (iii) a solution of rifaximin in methyl isobutylketone, with ethylacetate to form a second solution of rifaximin;
   filtering said second solution of rifaximin to obtain a filtered product; and
   drying the filtered product to obtain said crystalline form κ of rifaximin.

2. The process of claim 1, wherein said contacting said solid rifaximin or said solutions of rifaximin with ethylacetate occurs at a temperature in the range from 40 to 60° C.

3. The process of claim 2, wherein said ethylacetate which contacts said solution is at a temperature of 50° C.

4. The process of claim 1, wherein said solution of rifaximin is an ethylacetate solution.

5. An ethylacetate solvated rifaximin crystalline form characterized by a powder X-ray diffraction spectrum with peaks at values of angles 2θ of 5.23°, 6.70°, 7.57°, 8.09°, 8.49°, 8.95°, 11.78°, 12.08°, 13.17°, 14.62°, 14.80°, 15.78°, 16.24°, 16.64°, 19.13°, 21.38°, 23.70°.

6. A process for preparing the ethylacetate solvated rifaximin crystalline form of claim 5 comprising contacting solid rifaximin or a solution of rifaximin in ethylacetate with ethylacetate to yield a crystalline form of ethylacetated, solvated rifaximin and filtering the crystalline form therefrom.

\* \* \* \* \*